United States Patent
Min et al.

(10) Patent No.: US 11,903,733 B2
(45) Date of Patent: Feb. 20, 2024

(54) ELECTRONIC DEVICE FOR MEASURING BIO-SIGNALS

(71) Applicant: SAMSUNG ELECTRONICS CO., LTD., Suwon-si (KR)

(72) Inventors: Eungi Min, Suwon-si (KR); Inho Yun, Suwon-si (KR); Daniel Joe, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 362 days.

(21) Appl. No.: 17/094,272

(22) Filed: Nov. 10, 2020

(65) Prior Publication Data
US 2021/0153810 A1 May 27, 2021

(30) Foreign Application Priority Data
Nov. 22, 2019 (KR) .................. 10-2019-0151275

(51) Int. Cl.
| | |
|---|---|
| A61B 5/00 | (2006.01) |
| G06F 1/16 | (2006.01) |
| A61B 5/026 | (2006.01) |
| G01N 21/35 | (2014.01) |
| A61B 5/024 | (2006.01) |

(52) U.S. Cl.
CPC ............ *A61B 5/681* (2013.01); *A61B 5/0261* (2013.01); *A61B 5/02427* (2013.01); *A61B 5/742* (2013.01); *G01N 21/35* (2013.01); *G06F 1/163* (2013.01)

(58) Field of Classification Search
CPC ... A61B 5/02427; A61B 5/0261; A61B 5/681; A61B 5/742; G01N 21/35; G06F 1/163
See application file for complete search history.

(56) References Cited

U.S. PATENT DOCUMENTS

| | | |
|---|---|---|
| 10,215,698 B2 | 2/2019 | Han et al. |
| 10,241,033 B2 | 3/2019 | Uematsu et al. |

(Continued)

FOREIGN PATENT DOCUMENTS

| | | |
|---|---|---|
| KR | 10-2017-0003044 | 1/2017 |
| KR | 10-2017-0082255 | 7/2017 |

(Continued)

OTHER PUBLICATIONS

Extended European Search Report dated Oct. 27, 2022 for EP Application No. 20889480.8.

(Continued)

*Primary Examiner* — Christopher A Flory
(74) *Attorney, Agent, or Firm* — Nixon & Vanderhye P.C.

(57) ABSTRACT

In various embodiments, an electronic device may include: a light receiver including light receiving circuitry, a light emitter including light emitting circuitry, a partition wall disposed between the light receiver and the light emitter configured to block light emitted by the light emitter from being directly incident on the light receiver, a film disposed above one surface of the light receiver, and a processor. The film may include a transmission region configured to transmit light of all wavelength bands and a selective blocking region configured to absorb light of a specific wavelength band. The processor may be configured to analyze light incident on the light receiver through the film.

17 Claims, 14 Drawing Sheets

(56) References Cited

U.S. PATENT DOCUMENTS

| | | | |
|---|---|---|---|
| 2008/0259478 A1* | 10/2008 | Seo | G02B 1/111 |
| | | | 359/885 |
| 2013/0077284 A1* | 3/2013 | Chang | G02B 27/0101 |
| | | | 362/19 |
| 2013/0265522 A1* | 10/2013 | Jung | G02B 6/005 |
| | | | 428/524 |
| 2015/0342529 A1 | 12/2015 | Gassoway et al. | |
| 2016/0058375 A1 | 3/2016 | Rothkopf | |
| 2016/0103985 A1 | 4/2016 | Shim et al. | |
| 2016/0149132 A1* | 5/2016 | Lim | C09B 57/00 |
| | | | 546/268.1 |
| 2016/0198962 A1* | 7/2016 | Park | A61B 5/6843 |
| | | | 600/480 |
| 2016/0240721 A1 | 8/2016 | Chu et al. | |
| 2017/0154929 A1* | 6/2017 | Leem | H10K 85/653 |
| 2017/0249520 A1* | 8/2017 | Lee | H01L 27/14678 |
| 2017/0331050 A1* | 11/2017 | Yagi | C07D 471/04 |
| 2018/0098701 A1 | 4/2018 | Blomqvist et al. | |
| 2018/0148638 A1* | 5/2018 | Ahn | H10K 85/111 |
| 2018/0228414 A1 | 8/2018 | Shao et al. | |
| 2018/0317875 A1* | 11/2018 | Khayrullaev | A61B 5/7221 |
| 2018/0364869 A1* | 12/2018 | Lee | G06F 3/0421 |
| 2019/0076036 A1 | 3/2019 | Lasarov et al. | |
| 2019/0090806 A1 | 3/2019 | Clavelle et al. | |
| 2019/0231201 A1* | 8/2019 | Kano | A61B 5/7435 |
| 2019/0350464 A1 | 11/2019 | Jeon et al. | |
| 2020/0335211 A1* | 10/2020 | Gopalakrishnan | G16H 40/20 |
| 2020/0367827 A1 | 11/2020 | Min et al. | |

FOREIGN PATENT DOCUMENTS

| | | |
|---|---|---|
| KR | 10-2019-0064786 | 6/2019 |
| KR | 10-2146089 | 8/2020 |
| WO | WO 2019/107741 A1 | 6/2019 |

OTHER PUBLICATIONS

International Search Report dated Feb. 23, 2021 in corresponding International Application No. PCT/KR2020/015643.

* cited by examiner

ELECTRONIC DEVICE FOR MEASURING BIO-SIGNALS

CROSS-REFERENCE TO RELATED APPLICATION

This application is based on and claims priority under 35 U.S.C. § 119 to Korean Patent Application No. 10-2019-0151275, filed on Nov. 22, 2019, in the Korean Intellectual Property Office, the disclosure of which is incorporated by reference herein in its entirety.

BACKGROUND

Field

The disclosure relates to an electronic device for measuring bio-signals.

Description of Related Art

As interest in health increases, portable electronic devices provide functions capable of measuring user's bio-signals. Such bio-signals may be, for example, an electrocardiogram (ECG), an electroencephalography (EEG), an electromyography (EMG), and a heart rate (HR). The electronic device may measure and analyze such bio-signals and thereby provide user's biometric information such as a heart rate, the number of steps, a sleep state, stress information, body fat information, and calorie consumption.

The bio-signals can be measured through a sensor attached to a user's body, and the biometric information can be obtained by analyzing continuously measured bio-signals. Recently, various kinds of wearable electronic devices capable of measuring the bio-signals are being developed such as a wrist watch, a patch, glasses, a hat, a headband, an earphone, and a headset.

Among various biometric sensors, an optical heart-rate sensor may detect, through a light receiver thereof, light emitted by a light emitter thereof. Light emitted by the light emitter is incident on and reflected by a user's body, and the amount of reflected light is varied according to an increase or decrease in blood flow. Sensing this variation, the electronic device may calculate a user's heart rate.

The accuracy of the calculated heart rate depends on whether the electronic device accurately detects only the light reflected by the body. However, it may be difficult to accurately predict the path of light reflected by the body.

Thus, in order to accurately calculate the user's heart rate, the electronic device may restrict the path of light incident on the light receiver. However, if the electronic device detects only light incident on the light receiver through only a restricted angle to calculate the user's heart rate, the electronic device may fail to detect light, even reflected by the body, incident outside the restricted angle. In addition, the electronic device may be required to increase the area of the light receiver or use a plurality of light receivers so as to detect light incident outside the restricted angle.

SUMMARY

Embodiments of the disclosure may provide an electronic device for measuring bio-signals.

Embodiments of the disclosure provide an electronic device capable of blocking light of an undesired wavelength band while allowing light of a wavelength band used to measure a bio-signal to be incident on the light receiver without path restriction.

According to various example embodiments, an electronic device may include: a light receiver including light receiving circuitry, a light emitter including light emitting circuitry, a partition wall disposed between the light receiver and the light emitter configured to block light emitted by the light emitter from being directly incident on the light receiver, a film disposed above one surface of the light receiver, and a processor. The film may include a transmission region configured to transmit a light of all wavelength bands and a selective blocking region configured to absorb light of a specific wavelength band. The processor may be configured to analyze light incident on the light receiver through the film.

According to various example embodiments, light of a wavelength band used to measure a bio-signal may be incident without limiting a path.

In addition, a path of light of an undesired wavelength band may be selectively limited.

In addition, the accuracy of biometric information may be improved by measuring light of a wavelength band used to measure a bio-signal.

In addition, by selectively limiting the wavelength band of light, various bio-signals, such as an oxygen saturation, a heart rate, a blood pressure, and a blood sugar, may be measured for each wavelength band of light.

BRIEF DESCRIPTION OF THE DRAWINGS

The above and other aspects, features and advantages of certain embodiments of the present disclosure will be more apparent from the following detailed description, taken in conjunction with the accompanying drawings.

DETAILED DESCRIPTION

Hereinafter, various example embodiments of the disclosure will be described in greater detail with reference to the accompanying drawings.

Figure 1:
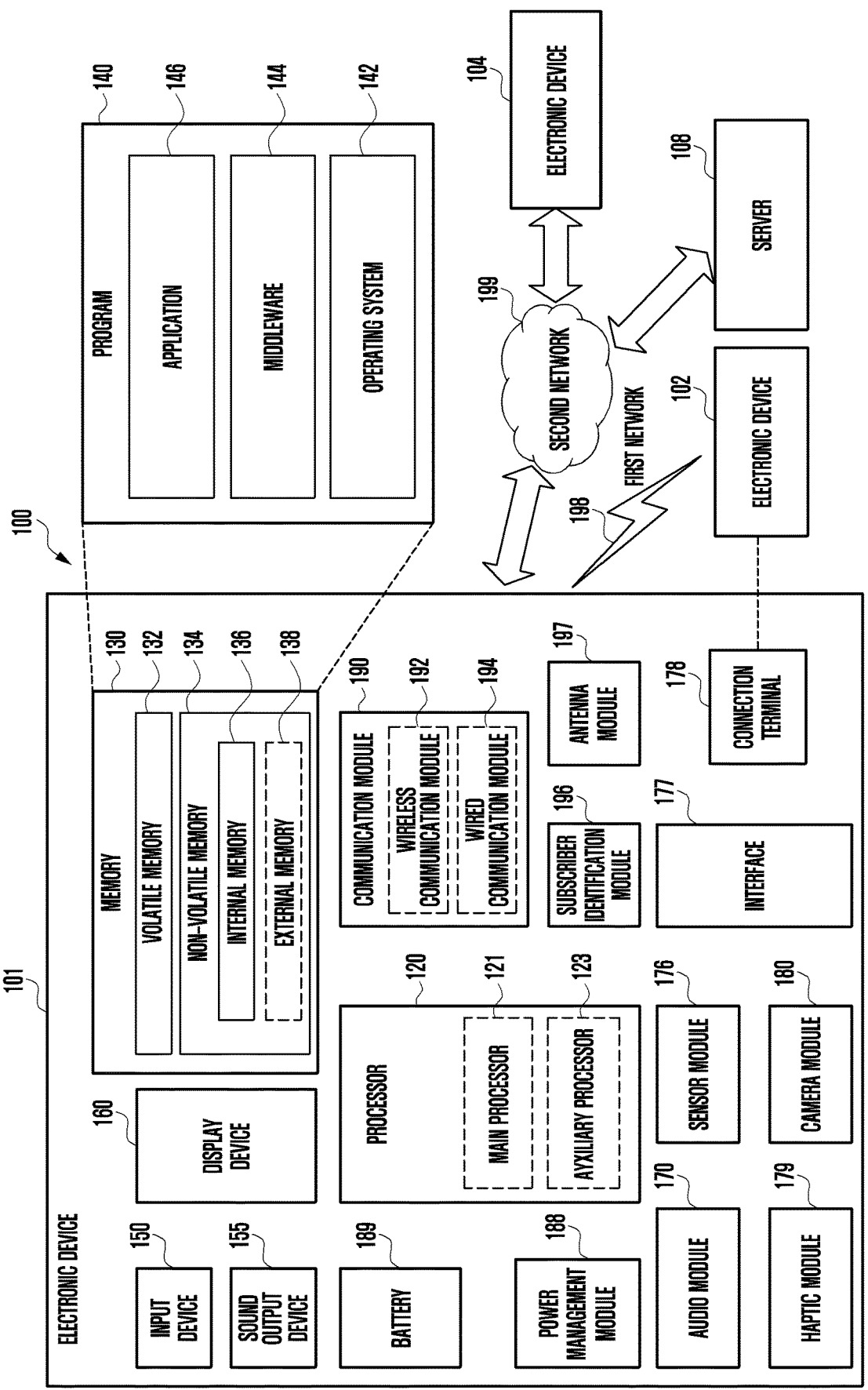
FIG. 1 is a block diagram illustrating an example electronic device in a network environment according to various embodiments.

FIG. 1 is a block diagram illustrating an example electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an example embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an example embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element include a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
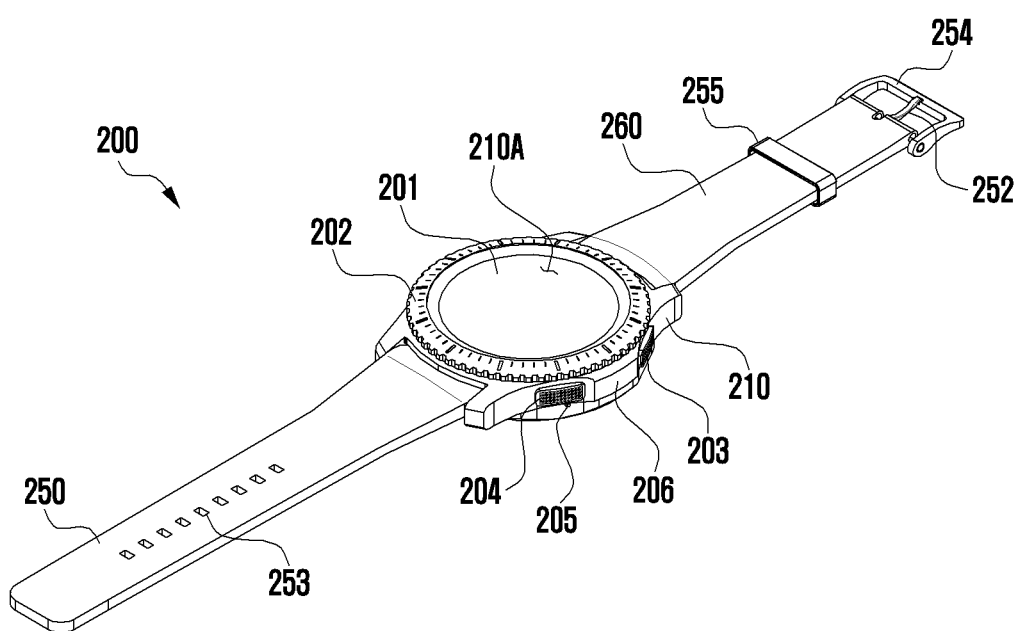
FIG. 2 is a front perspective view illustrating an example mobile electronic device according to various embodiments.
Figure 3:
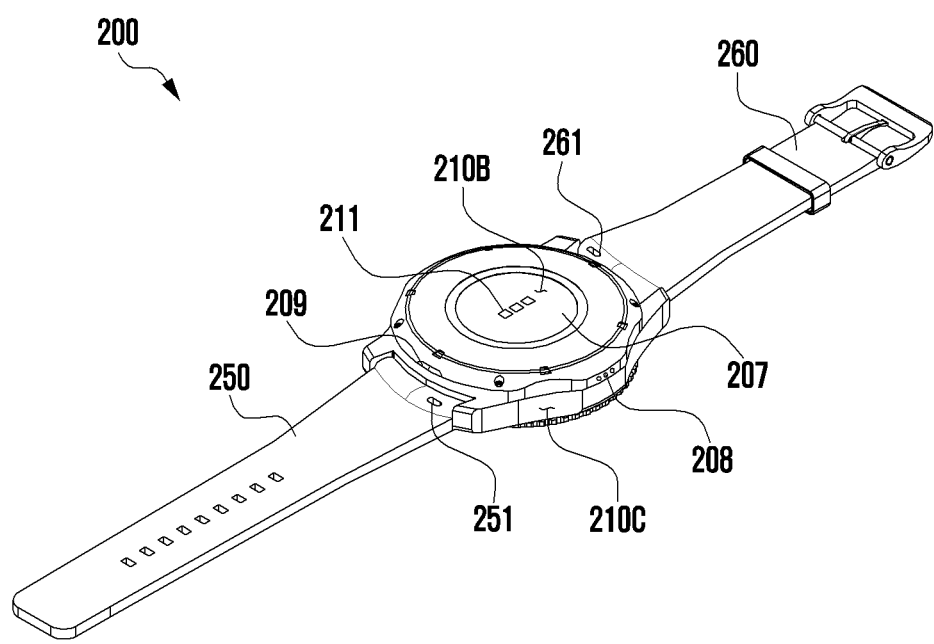
FIG. 3 is a rear perspective view illustrating of the electronic device shown in FIG. 2 according to various embodiments.
Figure 4:
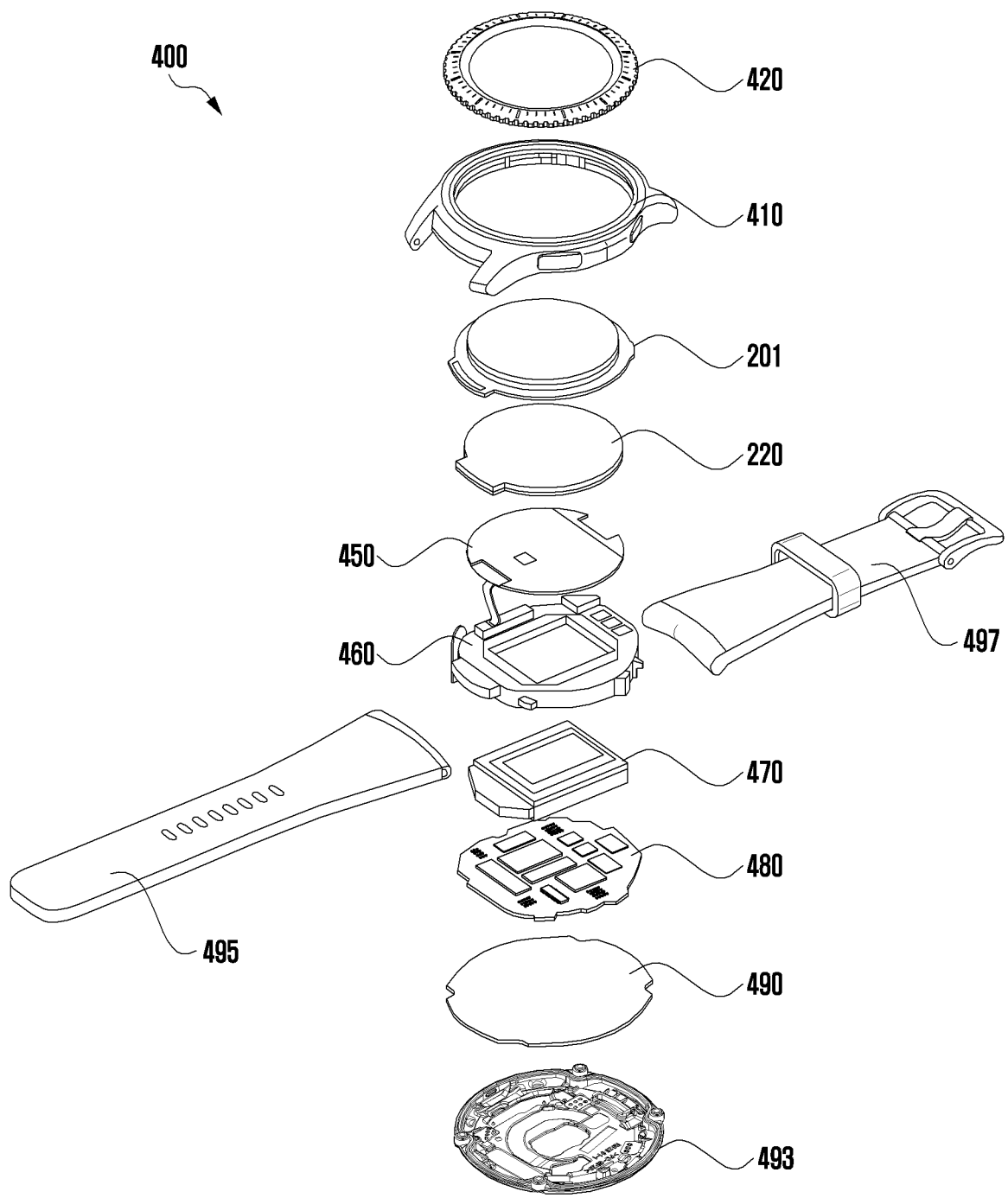
FIG. 4 is an exploded perspective view illustrating the electronic device shown in FIG. 2 according to various embodiments.

FIG. 2 is a perspective view illustrating a front face of a mobile electronic device according to various embodiments of the disclosure. FIG. 3 is a perspective view illustrating a rear face of the electronic device shown in FIG. 2. FIG. 4 is an exploded perspective view illustrating the electronic device shown in FIG. 2.

With reference to FIGS. 2 and 3, in an embodiment, the electronic device 200 may include: a housing 210 including a first surface (or, front surface) 210A, a second surface (or, rear surface) 210B, and a side surface 210C surrounding the space between the first surface 210A and the second surface 210B; and fastening members 250 and 260 (e.g., strap, connection member, or coupling member) connected to at least a portion of the housing 210 and configured to detachably fasten the electronic device 200 to a body part (e.g., wrist, ankle, etc.) of the user. In another embodiment (not shown), the housing 210 may refer to a structure forming some of the first surface 210A, the second surface 210B, and the side surface 210C in FIG. 2. In an embodiment, the first surface 210A may be formed by a front plate 201 that is substantially transparent at least in part (e.g., glass plate containing various coating layers, or polymer plate). The second surface 210B may be formed by a rear plate 207 that is substantially opaque. The rear plate 207 may be made of, for example, coated or colored glass, ceramic, polymer, metal (e.g., aluminum, stainless steel (STS), or magnesium), or a combination thereof. The side surface 210C is coupled to the front plate 201 and the rear plate 207 and may be formed by a side bezel structure (or, side member) 206 containing metal and/or polymer. In a certain embodiment, the rear plate 207 and the side bezel structure 206 may be integrally formed and contain the same material (e.g., metal material such as aluminum). The fastening members 250 and 260 may be made of various materials and formed in various shapes. The fastening members 250 and 260 may be formed as a single body or as plural unit links that are movable with each other, by woven material, leather, rubber, urethane, metal, ceramic, or a combination thereof.

In an embodiment, the electronic device 200 may include at least one of a display (e.g., display 220 in FIG. 4), an audio module (205 and 208), a sensor module 211, key input devices 202, 203 and 204, or a connector hole 209. In a certain embodiment, at least one of the components (e.g., key input device 202, 203 or 204, connector hole 209, and sensor module 211) may be removed from the electronic device 200, or a different component may be added to the electronic device 200.

The display can be viewed through, for example, a significant portion of the front plate 201. The display may have a shape corresponding to the shape of the front plate 201 and may have one of various shapes such as a circle, an ellipse, and a polygon. The display 220 may be disposed in combination with or adjacent to a touch sensing circuit, a pressure sensor capable of measuring the intensity (pressure) of a touch, and/or a fingerprint sensor.

The audio module (205 and 208) may include a microphone hole 205 and a speaker hole 208. In the microphone hole 205, a microphone for picking up external sounds may be disposed therein, and plural microphones may be arranged to sense the direction of sound in a certain embodiment. The speaker hole 208 can be used for an external speaker and a call receiver. In a certain embodiment, the speaker hole 208 and the microphone hole 205 may be implemented as a single hole, or a speaker (e.g., piezo speaker) may be included without the speaker hole 208.

The sensor module 211 may generate an electrical signal or data value corresponding to an internal operating state of the electronic device 200 or an external environmental state. The sensor module 211 may include, for example, a biometric sensor module 211 (e.g., HRM sensor) disposed on the second surface 210B of the housing 210. The electronic device 200 may further include a sensor module (not shown) including at least one of, for example, a gesture sensor, a gyro sensor, an air pressure sensor, a magnetic sensor, an acceleration sensor, a grip sensor, a color sensor, an infrared (IR) sensor, a biometric sensor, a temperature sensor, a humidity sensor, or an illuminance sensor.

The key input devices 202, 203 and 204 may include a wheel key 202 disposed on the first surface 210A of the housing 210 and rotatable in at least one direction, and/or side key buttons 203 and 204 disposed on the side surface 210C of the housing 210. The wheel key may have a shape corresponding to the shape of the front plate 201. In another embodiment, the electronic device 200 may not include some or all of the key input devices 202, 203 and 204 described above, and the key input device 202, 203 or 204 that is not included may be implemented in other forms, such as soft keys, on the display 220. The connector hole 209 may accommodate a connector (e.g., USB connector) for transmitting and receiving power and/or data to and from an external electronic device, and may include another connector hole (not shown) that can accommodate a connector for transmitting and receiving an audio signal to and from an external electronic device. The electronic device 200 may further include, for example, a connector cover (not shown) that covers at least a portion of the connector hole 209 and blocks foreign substances from entering the connector hole.

The fastening members 250 and 260 may be detachably fastened to at least a portion of the housing 210 by using locking members 251 and 261. The fastening members 250 and 260 may include one or more of a fixing member 252, fixing member fastening holes 253, a band guide member 254, and a band fixing ring 255.

The fixing member 252 may be configured to fix the housing 210 and the fastening members 250 and 260 to a body part (e.g., wrist, or ankle) of the user. The fixing member fastening holes 253 may fix the housing 210 and the fastening members 250 and 260 to a body part of the user in correspondence to the fixing member 252. The band guide member 254 may be configured to limit the range of movement of the fixing member 252 when the fixing member 252 engages with a fixing member fastening hole 253, so that the fastening members 250 and 260 may be fastened in close contact to a body part of the user. The band fixing ring 255 may limit the range of movement of the fastening members 250 and 260 while the fixing member 252 and the fixing member fastening hole 253 are fastened.

With reference to FIG. 4, the electronic device 400 may include a side bezel structure 410 (e.g., side member), a wheel key 420, a front plate 201, a display 220, a first antenna 450, a second antenna 455, a support member 460 (e.g., bracket), a battery 470, a printed circuit board 480, a sealing member 490, a rear plate 493, and fastening members 495 and 497 (or, mounting members). At least one of the components of the electronic device 400 may be identical or similar to at least one of the components of the electronic device 400 of FIGS. 2 and 3, and repeated descriptions are omitted herein. The support member 460 disposed inside the electronic device 400 may be formed to be connected to the side bezel structure 410 or be integrally formed with the side bezel structure 410. The support member 460 may be made of, for example, a metal material and/or a non-metal (e.g., polymer) material. The support member 460 may have one surface coupled to the display 220 and the other surface coupled to the printed circuit board 480. A processor, a memory, and/or an interface may be mounted on the printed circuit board 230. The processor may include one or more of, for example, a central processing unit, an application processor, a graphics processing unit (GPU), an application processor, sensor processor, and a communication processor.

The memory may include, for example, a volatile memory or a nonvolatile memory. The interface may include, for example, a high definition multimedia interface (HDMI), a universal serial bus (USB) interface, an SD card interface, and/or an audio interface. The interface allows the electronic device 200 to electrically or physically connect to an external electronic device, and may include, for example, a USB connector, an SD card/MMC connector, or an audio connector.

The battery 470 is a device for supplying power to at least one component of the electronic device 400, and may include, for example, a non-rechargeable primary cell, a rechargeable secondary cell, or a fuel cell. At least a portion of the battery 470 may be disposed substantially on the same plane as, for example, the printed circuit board 480. The battery 470 may be disposed as a single body within the electronic device 400 or may be detachably disposed from the electronic device 400.

The first antenna 450 may be disposed between the display 220 and the support member 460. The first antenna 450 may include, for example, a near field communication (NFC) antenna, a wireless charging antenna, and/or a magnetic secure transmission (MST) antenna. The first antenna 450, for example, may perform short-range communication with an external device, wirelessly transmit or receive power required for charging, and transmit a short-range communication signal or a magnetic-based signal including payment data. In another embodiment, an antenna structure may be formed by a side bezel structure 410 and/or a part of the support member 460 or a combination thereof.

The second antenna 455 may be disposed between the printed circuit board 480 and the rear plate 493. The second antenna 455 may include, for example, a near field communication (NFC) antenna, a wireless charging antenna, and/or a magnetic secure transmission (MST) antenna. The second antenna 455, for example, may perform short-range communication with an external device, wirelessly transmit or receive power required for charging, and transmit a short-range communication signal or a magnetic-based signal including payment data. In another embodiment, an antenna structure may be formed by a side bezel structure 410 and/or a part of the rear plate 493 or a combination thereof.

The sealing member 490 may be positioned between the side bezel structure 410 and the rear plate 493. The sealing member 490 may be configured to block moisture and foreign matter flowing into the space surrounded by the side bezel structure 410 and the rear plate 493 from the outside.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

Figure 5:
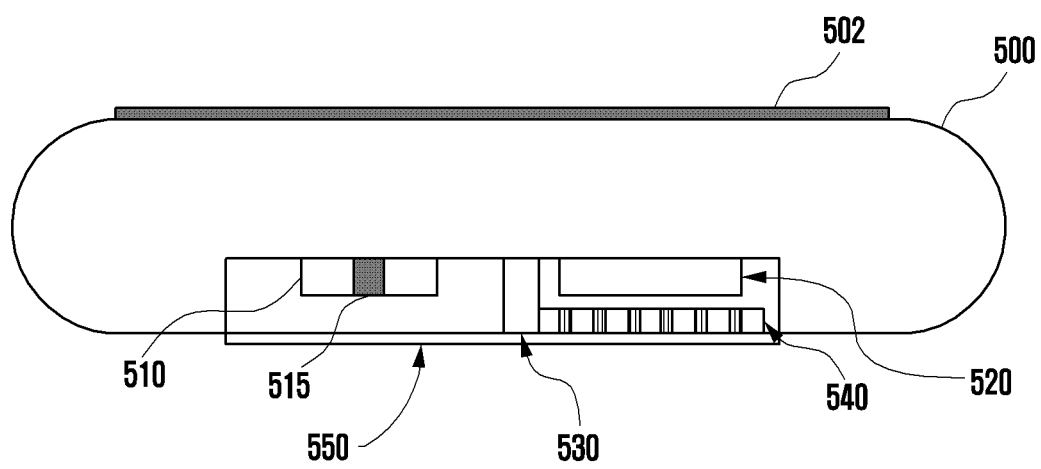
FIG. 5 is a diagram illustrating an example configuration of an electronic device according to various embodiments.

FIG. 5 is a diagram illustrating an example configuration of an electronic device according to various embodiments.

Referring to FIG. 5, the electronic device 500 (e.g., the electronic device 200 in FIG. 2) according to various embodiments may include a light emitter (e.g., including light emitting circuitry) 510 having a light source 515, a light receiver (e.g., including light receiving circuitry) 520, a partition wall 530, a film 540, and a window 550. According to various embodiments, at least some of the light emitter 510, the light receiver 520, the partition wall 530, the film 540, and the window 550 may be included in an optical sensor (e.g., the sensor module 211 in FIG. 3).

The light emitter 510 according to various embodiments may include various light emitting circuitry and the light source 515 capable of emitting light. For example, the light source 515 used for a heart rate sensor may be a green light emitting diode (green LED) that is relatively strong against noise. Additionally, a red LED, a blue LED, and/or an infrared ray (IR) LED may be used as the light source 515. The red LED and the IR LED may, for example, be used for measuring stress, oxygen saturation, and/or blood pressure, and the blue LED may, for example, be used for measuring blood sugar.

The light emitter 510 according to various embodiments may have a plurality of light sources, or a plurality of light emitters 510 may be included in the electronic device 500. According to various embodiments, depending on a bio-signal to be measured, a suitable light source capable of emitting one or more wavelength bands may be included in the electronic device 500.

According to various embodiments, light emitted by the light source 515 may be incident on the light receiver 520. The light receiver 520 may include at least one photodiode, for example. According to various embodiments, light emitted by the light source 515 may be incident on a user's body, then partially absorbed by the user's body, and partially reflected by the user's body. The reflected light may be incident on the light receiver 520.

According to various embodiments, the electronic device 500 may include the partition wall 530 that prevents, absorbs and/or blocks light emitted by the light emitter 515 from directly entering the light receiver 520. In addition, the partition wall 530 may absorb light incident from the outside. According to various embodiments, the partition wall 530 may include a material capable of absorbing light in all wavelength bands in addition to light emitted by the light source 515.

The film 540 according to various embodiments may selectively absorb light of a specific wavelength band. Because this light of a specific wavelength band absorbed by the film 540 cannot be incident on the light receiver 520, the film 540 may have an effect of blocking light of a specific wavelength band. According to various embodiments, the film 540 may include a transmission region and a selective blocking region. In the disclosure, the transmission region may refer, for example, to a region capable of passing light of all wavelength bands, and the selective blocking region may refer, for example, to a region capable of selectively absorbing light of a specific wavelength band and thereby selectively blocking light incident on the light receiver 520. According to various embodiments, the transmission region may include a transparent material, for example, a transparent epoxy. The selective blocking region may include a zinc-based material that absorbs light of a specific wavelength band.

The window 550 according to various embodiments may be used to protect a sensor. The window 550 may include a transparent glass or polycarbonate (PC) that transmits light of all wavelength bands.

The electronic device 500 according to various embodiments may further include a display 502 (e.g., the display 220 in FIG. 4). The display 502 may display (e.g., visually offer) biometric information obtained from analysis of the measured bio-signals.

The electronic device 500 according to various embodiments may further include a processor (e.g., the processor 120 in FIG. 1). The processor 120 may include various processing circuitry and analyze light incident on the light receiver 520. For example, the processor 120 may analyze the heart rate if light emitted by the light emitter 510 and incident on the light receiver 520 is green light, and may analyze the oxygen saturation in case of IR or red light. Also, the processor 120 may analyze the blood sugar in case of blue light.

According to various embodiments, the processor 120 may compare obtained biometric information of a user with stored biometric information of a normal person. If the obtained biometric information of the user is outside the range of the normal person, the processor 120 may transmit a notification to an external electronic device. For example, the notification may be sent to the user's family which is set in advance. According to various embodiments, the processor 120 may allow the user to designate biometric information for the notification.

According to various embodiments, when transmitting the notification, the processor 120 may also transmit location information of the electronic device 500.

The electronic device 500 according to various embodiments may further include a communication module (e.g., the communication module 190 in FIG. 1). The communication module 190 may include various communication circuitry and transmit the measured bio-signal or the analyzed biometric information to an external electronic device. The external electronic device may be an electronic device of any other user or another electronic device (e.g., a smartphone) of the user.

Figure 6:
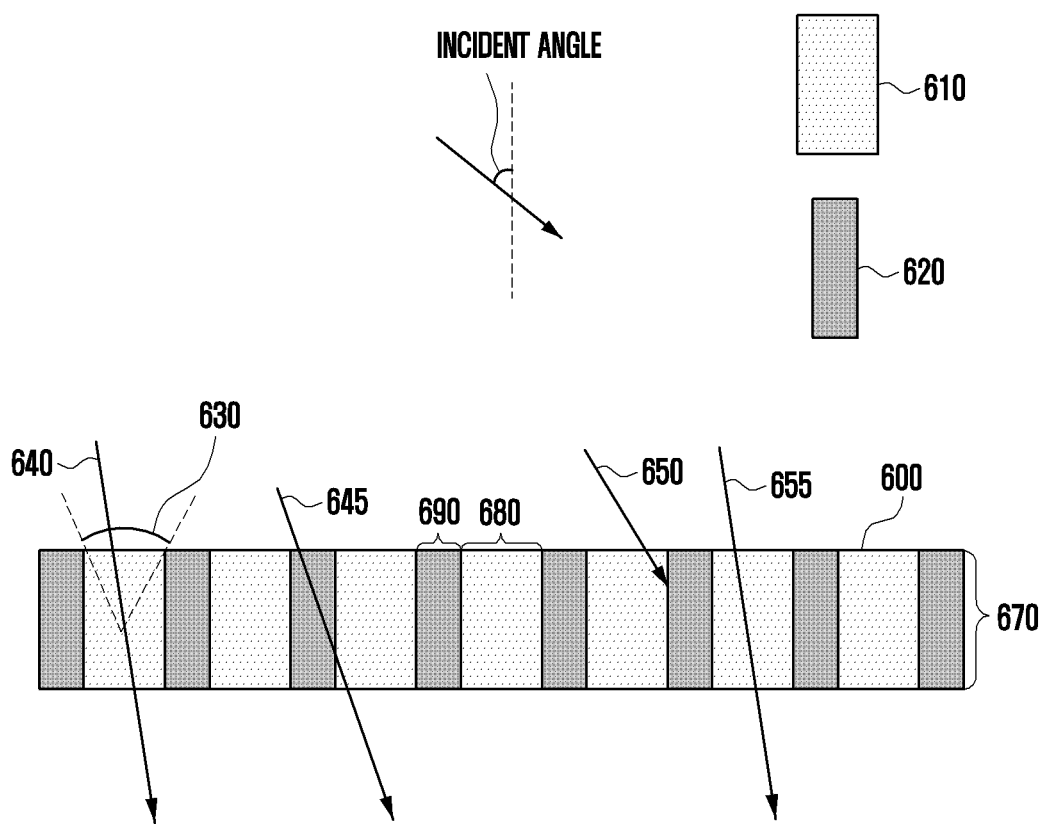
FIG. 6 is a cross-sectional view illustrating an example film for transmitting or blocking light according to various embodiments.

FIG. 6 is a cross-sectional view illustrating a film for transmitting or blocking/absorbing light according to various embodiments.

The film 600 (e.g., the film 540 in FIG. 5) according to various embodiments may include a transmission region 610 and a selective blocking/absorbing region 620. According to various embodiments, one film 600 may include a plurality of transmission regions 610 and a plurality of selective blocking regions 620. According to an embodiment, the transmission regions 610 and the selective blocking regions 620 may be alternately arranged, but are not limited thereto. According to an embodiment, the width 680 of the transmission region 610 and the width 690 of the selective blocking region 620 may be set differently.

Referring to FIG. 6, in the film 600, the arrangement structure of the transmission region 610 and the selective blocking region 620 may determine a restricted angle 630 that indicates the range of incident angles through which light can be transmitted. For example, if the selective blocking regions 620 may be sparsely arranged and thereby the width 680 of the transmission region 610 may be large, the restricted angle 630 may be large. On the other hand, if the selective blocking regions 620 are densely arranged and thereby the width 680 of the transmission region 610 is small, the restricted angle 630 may be small. According to an embodiment, the thickness 670 of the film 600 may also affect the restricted angle 630.

According to various embodiments, light of a wavelength band capable of passing through the selective blocking region 620 may pass through the film 600 regardless of the restricted angle 630 as indicated, for example, by reference numerals 640 and 645. On the other hand, as indicated, for example, by reference numeral 655, light of a wavelength band incapable of passing through the selective blocking region 620 can pass through the film 600 if the incident angle is smaller than the restricted angle 630. However, as exemplarily indicated by reference numeral 650, the light cannot pass through the film 600 if the incident angle is greater than the restricted angle 630.

According to various embodiments, the restricted angle 630 may be determined depending on the width 680 of the transmission region 610, the width 690 of the selective blocking region 620, and/or the thickness 670 of the film 600. As a result, a blocking rate of the film 600 may be determined. According to various embodiments, the restricted angle 630 may also be determined depending on a material of the selective blocking region 620, and the blocking rate of the film 600 may be determined accordingly.

Table 1 below illustrates example materials usable for the selective blocking region 620 and wavelengths of light that can be blocked by the respective materials.

TABLE 1

| Material of the selective blocking region 620 | Wavelength of light (nm) |
| --- | --- |
| $SNO_2$ | 326 |
| CeO | 388 |
| ZnO | 388 |
| $WO_3$ | 388 |
| $TiO_2$ | 388 |
| $SrTiO_3$ | 388 |
| SiC | 413 |
| CdS | 496 |
| $Fe_2O_3$ | 539 |
| GaP | 551 |
| CdSe | 730 |

For example, when the selective blocking region 620 is formed of CdS, light of the 496 nm wavelength band cannot pass through the film 600 because CdS absorbs such light.

Figure 7:
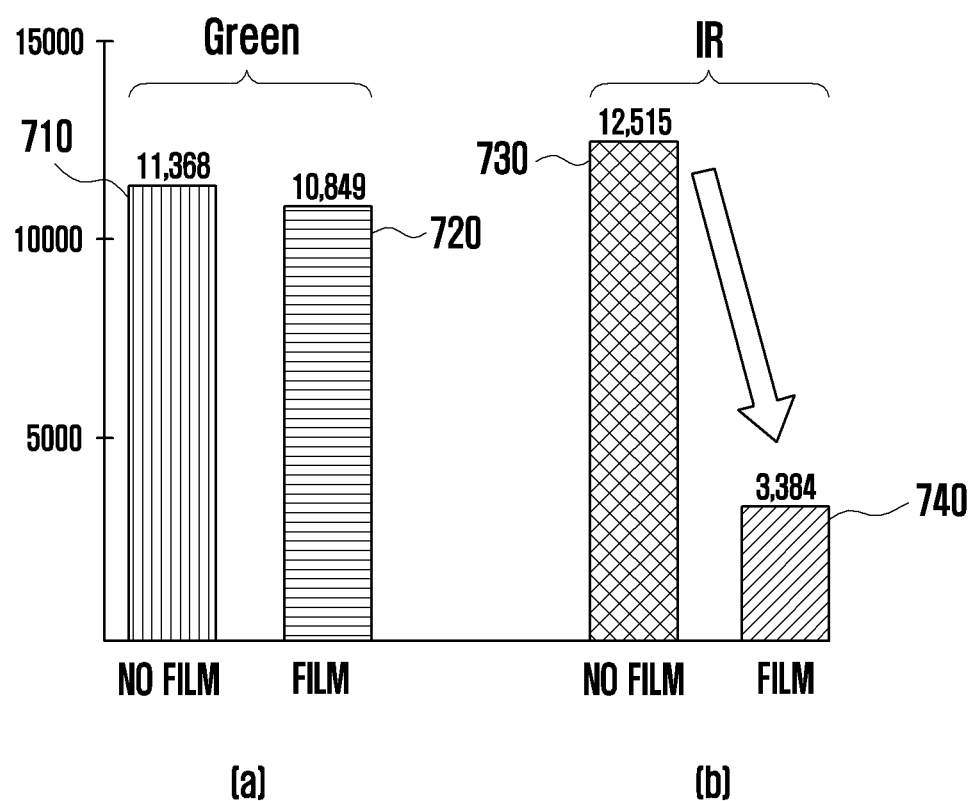
FIG. 7 is a graph illustrating an example result of simulating transmission or not of light through a film according to various embodiments.

FIG. 7 is a diagram illustrating an example result of simulating transmission or not of light through a film according to various embodiments.

For simulation of FIG. 7, the selective blocking region (e.g., the selective blocking region 620 in FIG. 6) included a material capable of absorbing about 820 nm wavelength, which belongs to an IR band, and the restricted angle (e.g., the restricted angle 630 in FIG. 6) was set to 30 degrees. In addition, one million photons were emitted for the simulation.

As shown in (a) of FIG. 7, light of a green wavelength (about 550 nm) band is capable of transmitting both the transmission region and the selective blocking region. As a result of simulation, it can be seen that 11,368 photons out of 1 million photons were incident on the light receiver in case of using no film as indicated by reference numeral 710, and 10,849 photons out of 1 million photons were incident on the light receiver in case of using a film as indicated by reference numeral 720. That is, in case of light of the green wavelength band, slightly more photons are incident on the light receiver when there is no film 710 than when there is a film 720, but the difference is only about 5%. Thus, in this case, the film hardly affects the performance.

On the other hand, as shown in (b) of FIG. 7, light of the IR wavelength band may be partially absorbed (e.g., blocked) by the selective blocking region of the film and thereby not be incident on the light receiver. As a result of simulation, it can be seen that 12,515 photons out of 1 million photons were incident on the light receiver in case of using no film as indicated by reference numeral 730, and 3,384 photons out of 1 million photons were incident on the light receiver in case of using a film as indicated by reference numeral 740. That is, in case of light of the IR wavelength band, the incident amount of photons was decreased by about 73% when there is a film 740 than when there is no film 730. Thus, in this case, the film blocks light of the IR wavelength band.

Figure 8:
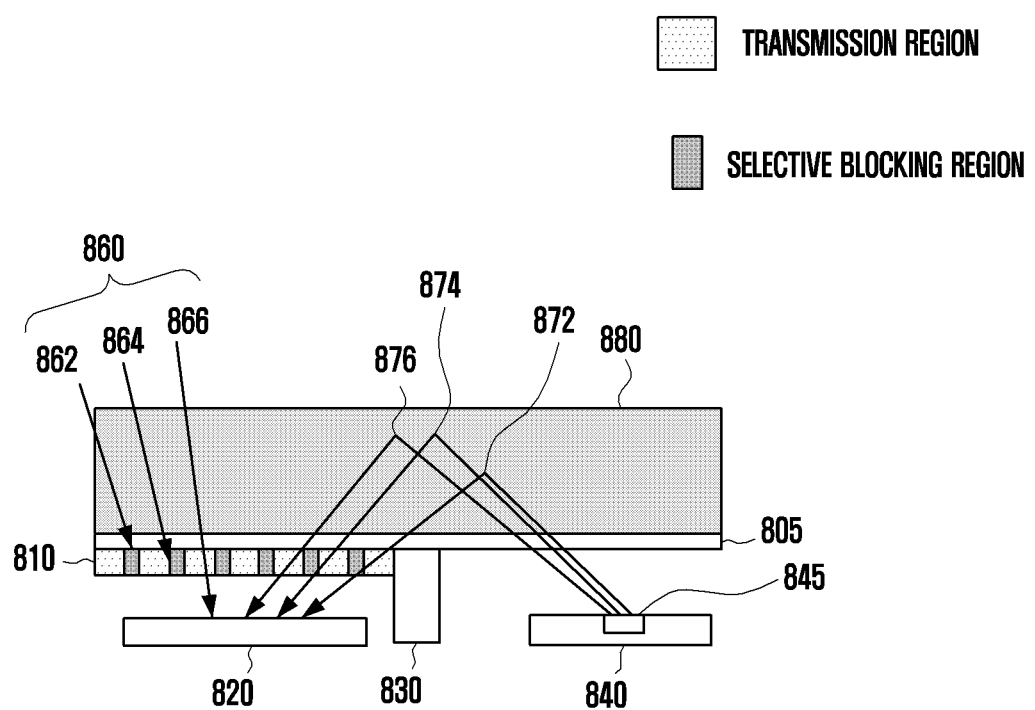
FIG. 8 is a diagram illustrating an example of measuring a bio-signal at an electronic device including a single light source according to various embodiments.

FIG. 8 is a diagram illustrating an example of measuring a bio-signal at an electronic device including a single light source according to various embodiments.

Referring to FIG. 8, the electronic device (e.g., the electronic device 500 in FIG. 5) according to various embodiments may include a window 805, a film 810, a light receiver 820, a partition wall 830, and a light emitter 840 including a light source 845.

The window 805 (e.g., the window 550 in FIG. 5) according to various embodiments may have one surface being in contact with a user's body 880, and the opposite surface on which the film 810 and the partition wall 830 are formed.

According to various embodiments, the film 810 may include a transmission region and a selective blocking region. External light 860 may pass through the body 880 and the film 810, and the selective blocking region of the film 810 may include a material capable of blocking red light, for example, out of the external light. According to various embodiments, only external light 866 incident within a restricted angle can pass through the film 810, and external light 862 or 864 incident greater than the restricted angle cannot be incident on the light receiver 820 by being absorbed by the selective blocking region of the film.

According to various embodiments, the light emitter 840 may include one light source 845.

According to various embodiments, the light source 845 may emit green light to measure the heart rate. The green light 872, 874, or 876 emitted by the light source 845 may be incident on the body 880 and then reflected to pass through the film 810. Having the wavelength band of 520 nm, the green light may not be absorbed by the selective blocking region of the film 810. The green light that has passed through the film 810 may be incident on the light receiver 820.

According to various embodiments, the partition wall 830 may prevent and/or absorb and/or block light emitted by the light source 845 from being directly incident on the light receiver 820. In order to prevent light of any wavelength band from being directly incident on the light receiver 820, the partition wall 830 may include a material that absorbs light in all wavelength bands.

Figure 9:
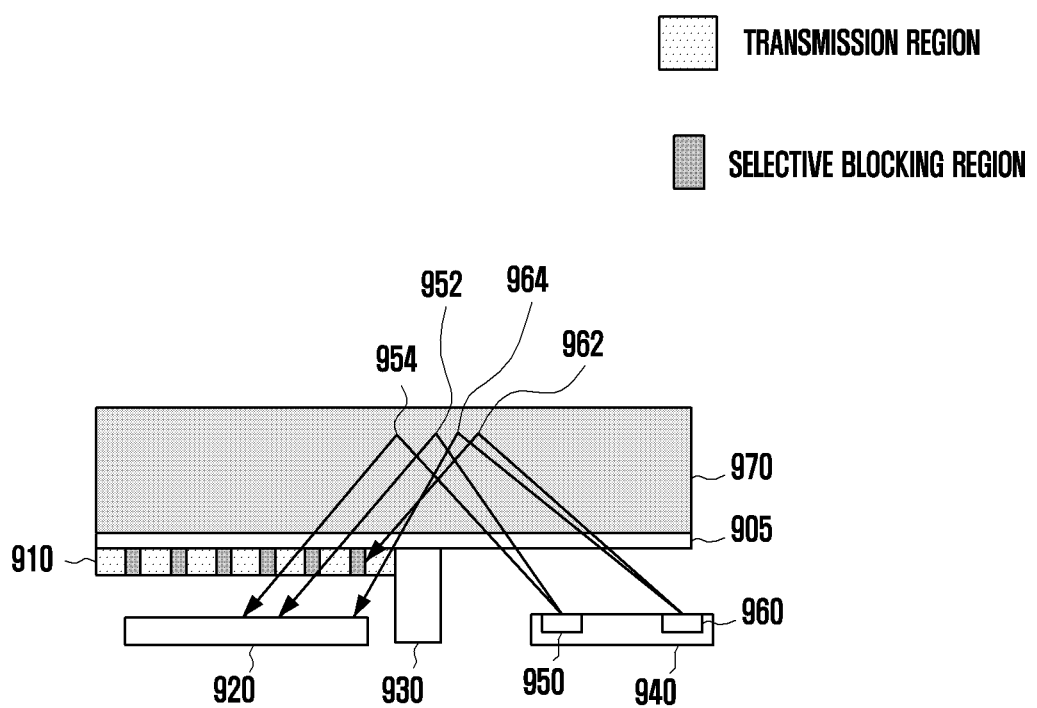
FIG. 9 is a diagram illustrating an example of measuring a bio-signal at an electronic device including a plurality of light sources according to various embodiments.

FIG. 9 is a diagram illustrating an example of measuring a bio-signal at an electronic device including a plurality of light sources according to various embodiments.

Referring to FIG. 9, the electronic device (e.g., the electronic device 500 in FIG. 5) according to various embodiments may include a window 905, a film 910, a light receiver 920, a partition wall 930, and a light emitter 940 including a plurality of light sources 950 and 960.

The window 905 and the partition wall 930 of FIG. 9 are the same or similar components as the window 805 and the partition wall 830 of FIG. 8, so that descriptions thereof will not be repeated here.

According to various embodiments, the light emitter 940 may include a plurality of light sources 950 and 960. For example, the first light source 950 may emit green light, and the second light source 960 may emit red light. Each light source may emit light of a wavelength band used to measure a bio-signal. Light emitted by each of the plurality of light sources 950 and 960 may be reflected after being incident on a body 970. At least part of the reflected light may be incident on the light receiver 920.

According to various embodiments, the film 910 may include a transmission region and a selective blocking region. The transmission region of the film 910 may pass all light irrespective of the wavelength band of the light. According to various embodiments, the selective blocking region of the film 910 may absorb light of a specific wavelength band. This gives the effect of blocking light of a specific wavelength band by the film 910. In FIG. 9, the selective blocking region of the film 910 may include a material capable of absorbing red light, for example. The selective blocking region of the film 910 may include, for example, CdSe. According to various embodiments, only red light 964 incident within the restricted angle can pass through the film 910, and red light 962 incident greater than the restricted angle cannot be incident on the light receiver 920 by being absorbed by the selective blocking region of the film 910. On the other hand, green light may not be absorbed by the selective blocking region of the film 910. For example, green light may pass through both the transmission region and the selective blocking region of the film 910, so that green light 952 or 954 can be incident on the light receiver 920 regardless of the restricted angle.

Figure 10:
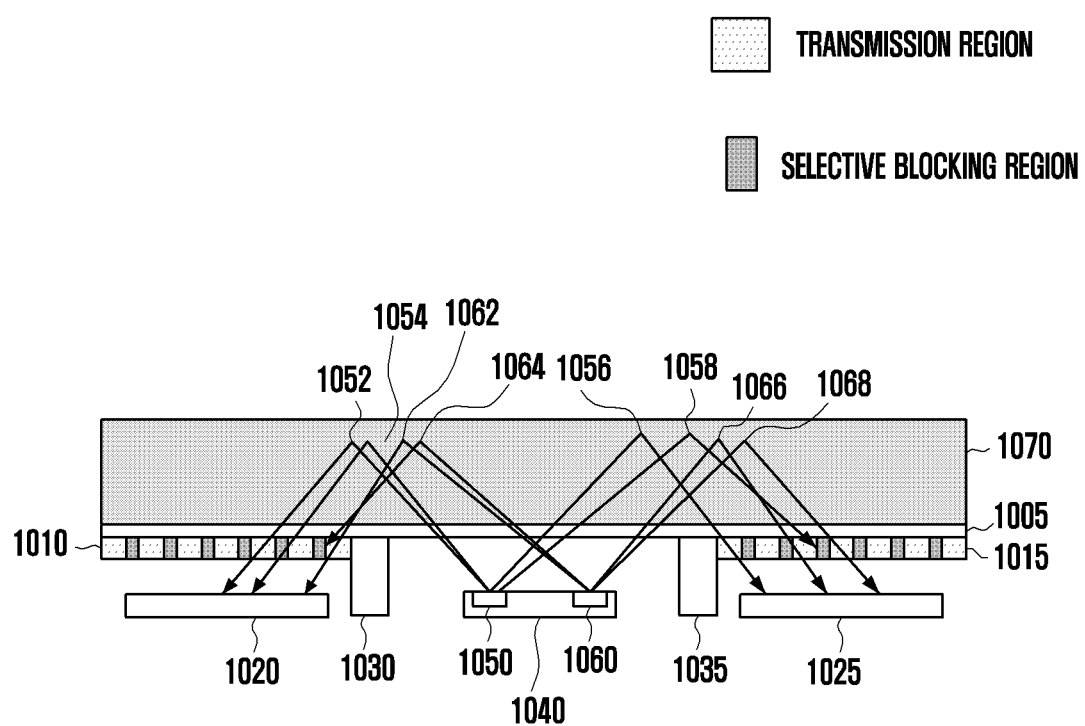
FIG. 10 is a diagram illustrating an example of measuring a bio-signal at an electronic device including a plurality of light sources and a plurality of light receivers according to various embodiments.

FIG. 10 is a diagram illustrating an example of measuring a bio-signal at an electronic device including a plurality of light sources and a plurality of light receivers according to various embodiments.

Referring to FIG. 10, the electronic device (e.g., the electronic device 500 in FIG. 5) according to various embodiments may include a window 1005, a plurality of films 1010, 1015 a plurality of light receivers 1020, 1025 a plurality of partition walls 1030, 1035 and a light emitter 1040.

The light emitter 1040 may include a plurality of light sources 1050 and 1060, and is the same or similar component as the light emitter 940 of FIG. 9, and descriptions thereof will not be repeated here.

According to various embodiments, in order to prevent light emitted by the light sources 1050 and 1060 from being directly incident on the light receivers 1020 and 1025, the partition walls 1030 and 1035 may be disposed between the light emitter 1040 and each of the light receivers 1020 and 1025.

According to various embodiments, the electronic device 500 may include the plurality of light receivers 1020 and 1025. Without a film, light of all wavelength bands may be incident on the plurality of light receivers 1020 and 1025.

According to various embodiments, different films 1010 and 1015 for blocking light of different wavelength bands may be disposed in front of the light receivers 1020 and 1025, respectively. For example, the first film 1010 disposed in front of the first light receiver 1020 may include a selective blocking region, which may include a material that absorbs red light. In addition, the second film 1015 disposed in front of the second light receiver 1025 may also include a selective blocking region, which may include a material that absorbs green light. The green light 1052 or 1054 emitted by the first light source 1050 and then incident on and reflected by the body 1070 may pass through the first film 1010, but such green light 1056 or 1058 may fail to pass through some regions of the second film 1015. In addition, the red light 1066 or 1068 emitted by the second light source 1060 and then incident on and reflected by the body 1070 may pass through the second film 1015, but such red light 1062 or 1064 may fail to pass through some regions of the first film 1010.

According to various embodiments, the electronic device 500 may measure a user's heart rate by analyzing green light incident on the first light receiver 1020, and also measure a user's oxygen saturation by analyzing red light incident on the second light receiver 1015.

Figure 11:
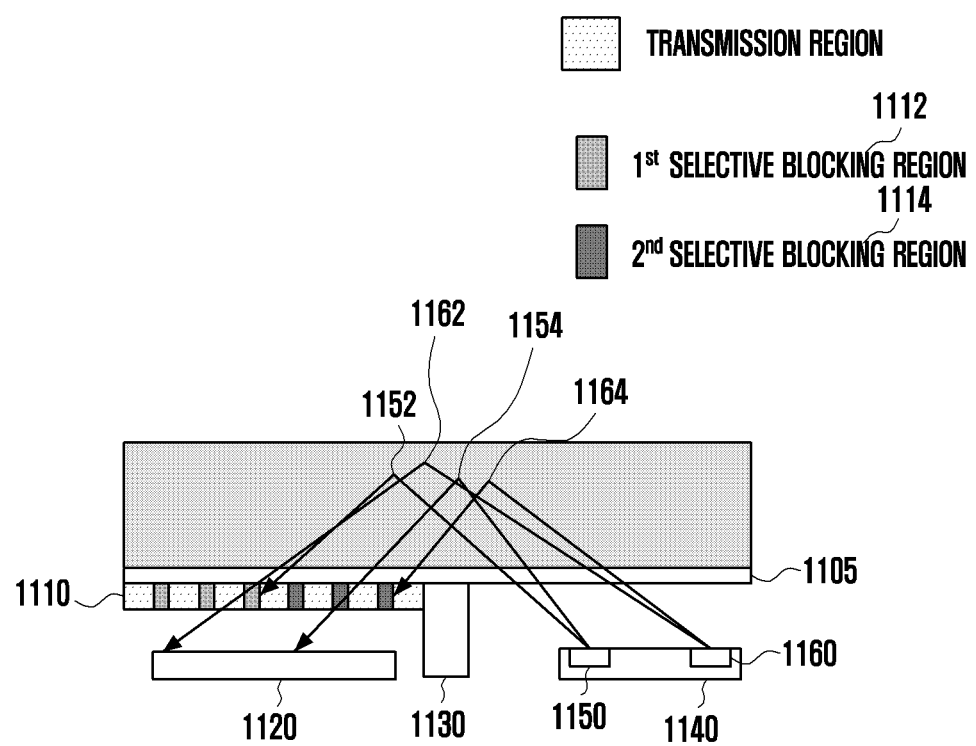
FIG. 11 is a diagram illustrating an example of measuring a bio-signal by blocking a plurality of lights through a plurality of selective blocking regions according to various embodiments.

FIG. 11 is a diagram illustrating an example of measuring a bio-signal by blocking a plurality of different wavelengths of light through a light receiver according to various embodiments.

Referring to FIG. 11, the electronic device (e.g., the electronic device 500 in FIG. 5) according to various embodiments may include a window 1105, a film 1110, a light receiver 1120, a partition wall 1130, and a light emitter 1140 including a plurality of light sources 1150 and 1160.

The window 1105, the light receiver 1120, the partition wall 1130, and the plurality of light sources 1150 and 1160 of FIG. 11 are the same or similar components as the window 905, the light receiver 920, the partition wall 930, and the plurality of light sources 950 and 960 of FIG. 9, and descriptions thereof may not be repeated here.

According to various embodiments, the film 1110 may include a transmission region and a selective blocking region. In order to block light in a plurality of wavelength bands, a plurality of selective blocking regions, for example, first and second selective blocking regions 1112 and 1114, may be included in one film 1110. The first selective blocking region 1112 may include a material capable of absorbing green light, thereby blocking green light 1152 and transmitting red light 1162. The second selective blocking region 1114 may include a material capable of absorbing red light, thereby blocking red light 1164 and transmitting green light 1154.

Figure 12:
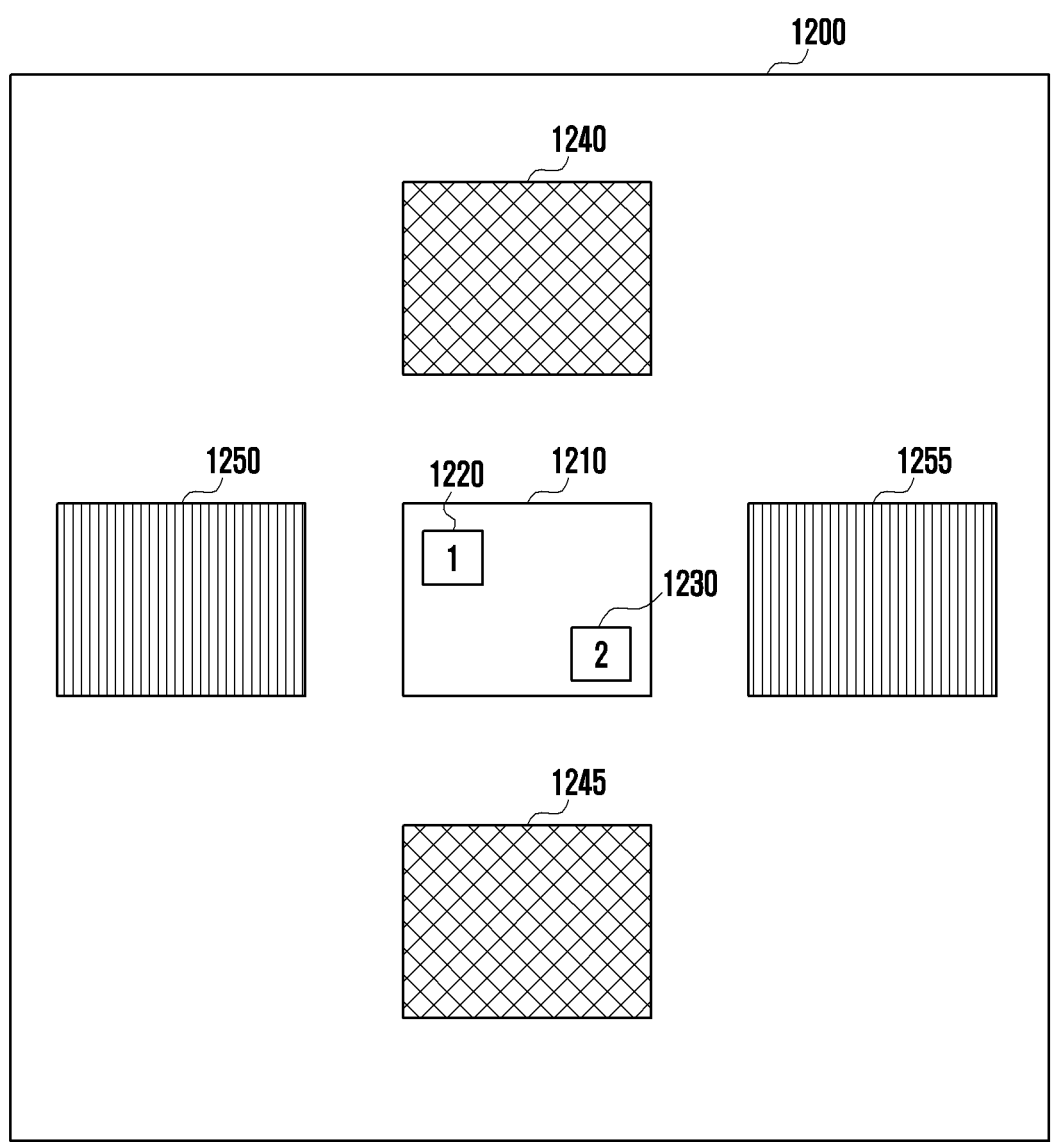
FIG. 12 is a diagram illustrating an example of measuring a bio-signal using a plurality of light receivers according to various embodiments.

FIG. 12 is a diagram illustrating an example of measuring a bio-signal using a plurality of light receivers according to various embodiments.

According to various embodiments, a light emitter 1210 may include a plurality of light sources, for example, first and second light sources 1220 and 1230. The first light source 1220 may emit green light, and the second light source 1230 may emit red light.

According to various embodiments, an electronic device 1200 (e.g., the electronic device 500 in FIG. 5) may measure a bio-signal at a plurality of locations in order to increase the accuracy of biometric information. FIG. 12 exemplarily shows that four light receivers 1240, 1245, 1250, and 1255 are disposed to measure a bio-signal at a plurality of locations. A film (not shown) may be disposed above one surface of each light receiver.

According to various embodiments, green light may be incident on the first light receiver 1240 and the second light receiver 1245, and red light may be incident on the third light receiver 1250 and the fourth light receiver 1255. In order to allow light of different wavelengths to pass through, a film disposed in front of the first and second light receivers 1240 and 1245 and a film disposed in front of the third and fourth light receivers 1250 and 1255 may be different from each other. For example, a material of a selective blocking region contained in the film disposed in front of the first and second light receivers 1240 and 1245 and a material of a selective blocking region contained in the film disposed in front of the third and fourth light receivers 1250 and 1255 may be different from each other.

According to various embodiments, even if the selective blocking region of the film disposed in front of the first and second light receivers 1240 and 1245 is formed of the same material, the selective blocking region corresponding to the first light receiver 1240 and the selective blocking region corresponding to the second light receiver 1245 may have different characteristics. For example, the film disposed in front of the first light receiver 1240 and the film disposed in front of the second light receiver 1245 may have different restricted angles. In another example, the film disposed in front of the first light receiver 1240 and the film disposed in front of the second light receiver 1245 may be different in thickness from each other.

Hereinafter, a description will be made focusing on the film disposed above one surface of the light receiver.

Figure 13:
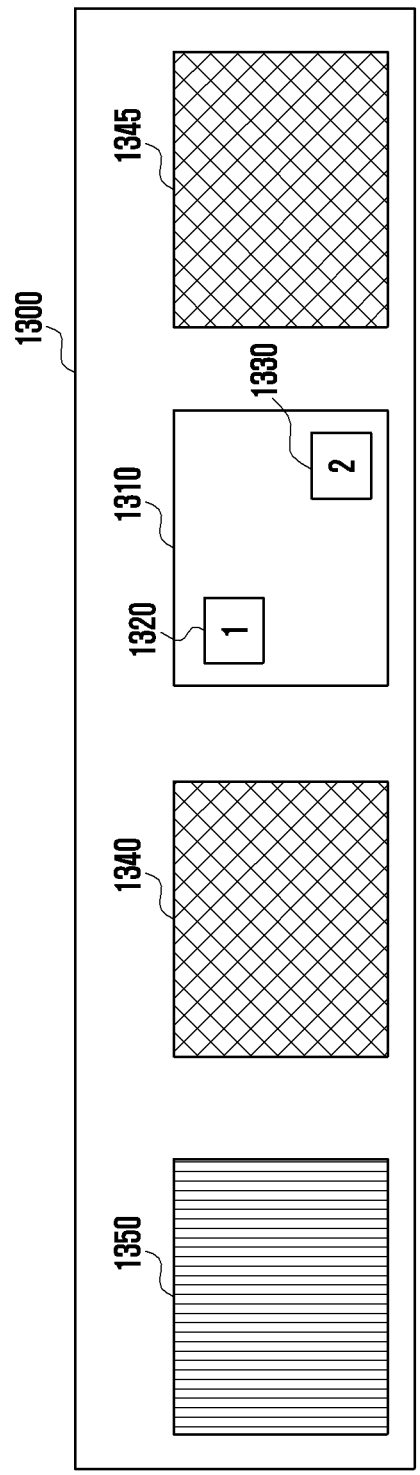
FIG. 13 is a diagram illustrating an example of measuring a bio-signal using a plurality of light receivers according to various embodiments.

FIG. 13 is a diagram illustrating an example of measuring a bio-signal by using a plurality of light receivers according to various embodiments.

Referring to FIG. 13, an electronic device 1300 (e.g., the electronic device 500 in FIG. 5) according to various embodiments may include one light emitter 1310, which may include a plurality of light sources 1320 and 1330.

According to various embodiments, the light emitter 1310 and a plurality of light receivers (not shown) may be arranged in a line. In addition, a plurality of films 1340, 1345, and 1350 may be disposed above one surface of the plurality of light receivers, respectively.

According to various embodiments, the first light source 1320 may emit green light, and the second light source 1330 may emit red light. According to various embodiments, light emitted by the first light source 1320 may pass through the first film 1340 and the second film 1345, and light emitted by the second light source 1330 may pass through the third film 1350. According to various embodiments, the first film 1340 and the second film 1345 may absorb light emitted by the second light source 1330, and the third film 1350 may absorb light emitted by the first light source 1320. According to various embodiments, the film disposed closer to the edge of the electronic device 1300 may absorb more external light.

Figure 14:
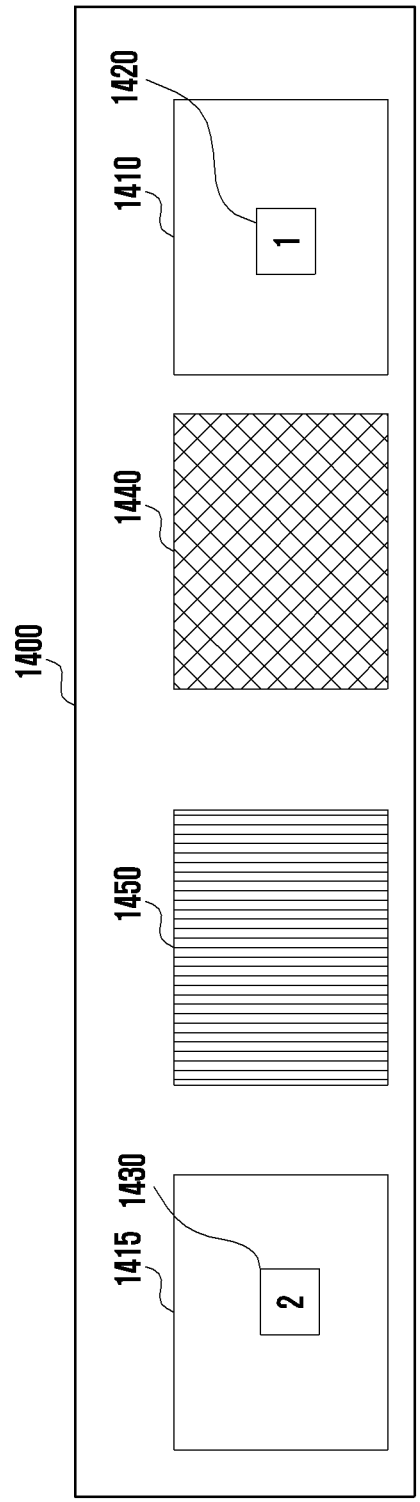
FIG. 14 is a diagram illustrating an example of measuring a bio-signal using a plurality of light receivers according to various embodiments.

FIG. 14 is a diagram illustrating an example of measuring a bio-signal by using a plurality of light receivers according to various embodiments.

Referring to FIG. 14, an electronic device 1400 (e.g., the electronic device 500 in FIG. 5) according to various embodiments may include a plurality of light emitters 1410 and 1415. Each of the plurality of light emitters 1410 and 1415 may include a light source 1420 or 1430. In addition, the electronic device 1400 may include a plurality of light receivers (not shown) for receiving light emitted by the light sources 1420 and 1430, and also include a plurality of films 1440 and 1450 disposed above one surface of the plurality of light receivers, respectively. For example, when the first light source 1420 emits green light and the second light source 1430 emits red light, the first film 1440 may transmit green light and absorb red light, and the second film 1450 may transmit red light and absorb green light. In this case, the selective blocking region of the first film 1440 may include a material that absorbs red light, so that the blocking rate of red light may be improved for the light receiver covered with the first film 1440. Similarly, the selective blocking region of the second film 1450 may include a material that absorbs green light, so that the blocking rate of green light may be improved for the light receiver covered with the second film 1450. According to various embodiments, in the first film 1440 and the second film 1450, the transmission regions may include the same material, but the selective blocking regions may include different materials.

The light emitter(s), the light receiver(s), and the film(s), described above, are illustrative, non-limiting examples only. According to various embodiments, a plurality of light emitters and a plurality of light receivers may be variously disposed, and a plurality of films disposed above the plurality of light receivers may also be variously configured. For example, even in case of a film used to allow light of the same wavelength to be incident, the thickness and/or width of the film may be varied to change the restricted angle, and the transmission region and the selective blocking region may be arranged in various ways. According to various embodiments, materials forming the transmission region and the selective blocking region may be various.

According to various example embodiments of the disclosure, an electronic device may include: a light receiver including light emitting circuitry, a light emitter including light emitting circuitry, a partition wall disposed between the light receiver and the light emitter configured to block light emitted by the light emitter from being directly incident on the light receiver, a film disposed above one surface of the light receiver, and a processor. The film may include a transmission region for transmitting light of all wavelength bands and a selective blocking region for absorbing light of a specific wavelength band. The processor may analyze light incident on the light receiver through the film.

In the electronic device according to various example embodiments, the specific wavelength band may be a wavelength band of external light.

In the electronic device according to various example embodiments, the light emitter may emit green light, the selective blocking region of the film may absorb red light, and the processor may analyze a heart rate using the green light incident on the light receiver through the film.

In the electronic device according to various example embodiments, the light emitter may emit red light and/or infrared light, and the processor may analyze an oxygen saturation \using the red light and/or the infrared light incident on the light receiver through the film.

In the electronic device according to various example embodiments, the light emitter may emit blue light, the selective blocking region of the film may absorb red light, and the processor may analyze a blood sugar level using the blue light incident on the light receiver through the film.

In the electronic device according to various example embodiments, a blocking rate may be determined based on a material comprising the selective blocking region.

In the electronic device according to various example embodiments, in the film, the transmission region and the selective blocking region may be alternately arranged.

In the electronic device according to various example embodiments, in the film, an arrangement structure of the transmission region and the selective blocking region may be arranged to determine a restricted angle.

In the electronic device according to various example embodiments, the restricted angle may be further determined based on a thickness of the film.

In the electronic device according to various example embodiments, the light receiver may include a plurality of light receivers, and the film may include a plurality of films disposed above the plurality of light receivers, respectively.

In the electronic device according to various example embodiments, the selective blocking region included in at least one of the plurality of films may include a material different from a material of the selective blocking region included in others of the plurality of films.

In the electronic device according to various example embodiments, the light emitter may be configured to emit light of two type wavelength bands, the light receiver may include at least two light receivers, and the film disposed above at least one of the at least two light receivers may absorb one of the light of two type wavelength bands.

In the electronic device according to various example embodiments, the light emitter may emit light of two type wavelength bands, the film disposed above the light receiver may include a plurality of selective blocking regions, and at least one of the plurality of selective blocking regions may absorb one of the light of two type wavelength bands.

In the electronic device according to various example embodiments, the selective blocking region may include a plurality of selective blocking regions, and at least one of the plurality of selective blocking regions may be different in a material from others of the plurality of selective blocking regions.

In the electronic device according to various example embodiments of the disclosure, the selective blocking region may include a plurality of selective blocking regions, and at least one of the plurality of selective blocking regions may have a different distance from the transmission region.

The electronic device according to various example embodiments may further include a display configured to display biometric information obtained from analysis by the processor.

In the electronic device according to various example embodiments of the disclosure, the processor may be configured to control the display to display a notification based on the obtained biometric information being outside a range of a normal person.

The electronic device according to various example embodiments may further include a communication module including communication circuitry, and the processor may be configured to control the communication module to transmit the obtained biometric information to an external electronic device.

In the electronic device according to various example embodiments, the external electronic device may be predetermined.

In the electronic device according to various example embodiments, the processor may be further configured to control the communication module to transmit location information of the electronic device.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used herein, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been illustrated and described with reference to various example embodiments, it will be understood that the various example embodiments are intended to be illustrative, not limiting. It will be further understood by one of ordinary skill in the art that various changes in form and detail may be made without departing from the true spirit and full scope of the disclosure, including the appended claims and their equivalents.

What is claimed is:

1. An electronic device comprising:
   a first light receiver including first light receiving circuitry;
   a second light receiver including second light receiving circuitry;
   a light emitter including light emitting circuitry configured to emit light in a first wavelength band and to emit light in a second wavelength band;
   a plurality of partition walls disposed between the first light receiver and the light emitter and between the second light receiver and the light emitter configured to block light emitted by the light emitter from being directly incident on the first and the second light receivers;
   a first film disposed above one surface of the first light receiver;
   a second film disposed above one surface of the second light receiver; and
   a processor,
   wherein the first film includes a transmission region configured to transmit light of all wavelength bands and a selective blocking region configured to absorb light of wavelength bands other than the first wavelength band,
   wherein the second film includes a transmission region configured to transmit light of all wavelength bands and a selective blocking region configured to absorb light of wavelength bands other than the second wavelength band, and
   wherein the processor is configured to analyze light incident on the first and second light receivers through the first and second films.

2. The electronic device of claim 1, wherein the selective blocking regions of the first and second film are configured to absorb a specific wavelength band of light generated external to the electronic device.

3. The electronic device of claim 2, wherein the light emitter is configured to emit green light,
   wherein the selective blocking region of the first film is configured to absorb red light, and
   wherein the processor is configured to analyze a heart rate using the green light incident on the first light receiver through the first film.

4. The electronic device of claim 2, wherein the light emitter is configured to emit red light and/or infrared light, and
   wherein the processor is configured to analyze an oxygen saturation using the red light and/or the infrared light incident on the second light receiver through the second film.

5. The electronic device of claim 2, wherein the light emitter is configured to emit blue light,
   wherein the selective blocking region of the first film is configured to absorb red light, and
   wherein the processor is configured to analyze a blood sugar level using the blue light incident on the first light receiver through the first film.

6. The electronic device of claim 1, wherein a blocking rate is determined based on a material of the selective blocking region.

7. The electronic device of claim 1, wherein in the first and second films, the transmission region and the selective blocking region are alternately arranged.

8. The electronic device of claim 7, wherein in the first and second films, an arrangement of the transmission region and the selective blocking region determines a restricted angle.

9. The electronic device of claim 8, wherein the restricted angle is further determined based on a thickness of the first and second films.

10. The electronic device of claim 1, wherein the selective blocking region included in the first film includes a material different from a material of the selective blocking region included in the second film.

11. The electronic device of claim 1, wherein the selective blocking region of the first film and/or the second film includes a plurality of selective blocking regions.

12. The electronic device of claim 1, wherein the selective blocking region of at least one of the first and second films includes a plurality of selective blocking regions, and
wherein the plurality of selective blocking regions are disposed at a different distances from the transmission region.

13. The electronic device of claim 1, further comprising:
a display configured to display biometric information obtained from analysis by the processor.

14. The electronic device of claim 13, wherein the processor is configured to control the display to display a notification based on the obtained biometric information being outside a normal range.

15. The electronic device of claim 1, further comprising:
a communication module including communication circuitry,
wherein the processor is configured to control the communication module to transmit the obtained biometric information to an external electronic device.

16. The electronic device of claim 15, wherein the external electronic device is predetermined.

17. The electronic device of claim 15, wherein the processor is further configured to control the communication module to transmit location information of the electronic device.

* * * * *